United States Patent [19]
Wallach

[11] 3,949,746
[45] Apr. 13, 1976

[54] ANIMAL INJECTOR APPARATUS
[75] Inventor: Mark Wallach, New York, N.Y.
[73] Assignee: Animal Systems, Inc., Branson, Mo.
[22] Filed: Sept. 3, 1974
[21] Appl. No.: 502,800

[52] U.S. Cl..... 128/218 G; 128/218 A; 128/218 M; 141/243; 141/258; 141/329
[51] Int. Cl.[2]........................................ A61M 5/00
[58] Field of Search... 128/2 R, 2.05 R, 213, 214 R, 128/214 F, 214 E, 214.2, 215–218 R, 218 M, 218 N, 218 A, 218 G, 218 S, 221–223, 230, 234–237, 247, 253, 273, DIG. 1, DIG. 7, DIG. 10, 347–349; 222/80–83, 129, 132, 135, 252, 309, 333, 41; 141/104, 243, 258, 329

[56] References Cited
UNITED STATES PATENTS

| 1,316,394 | 9/1919  | Sellar     | 128/218 N |
| 2,457,977 | 1/1949  | Cookson    | 128/218 A |
| 2,727,512 | 12/1955 | Muller     | 128/214   |
| 2,764,980 | 10/1956 | Smith      | 128/218 A |
| 2,896,621 | 7/1959  | Rodrigues  | 128/218 A |
| 3,016,897 | 1/1962  | Kendrick   | 128/218 G |
| 3,302,645 | 2/1967  | Lockmiller | 128/223   |
| 3,335,724 | 8/1967  | Gienapp    | 128/273   |
| 3,509,880 | 5/1970  | Guttman    | 128/347   |
| 3,530,492 | 9/1970  | Ferber     | 128/347   |
| 3,572,336 | 3/1971  | Hershberg  | 128/218 M |

Primary Examiner—John D. Yasko
Attorney, Agent, or Firm—Howard C. Miskin

[57] ABSTRACT

A hypodermic syringe apparatus includes a contact member having an apertured front plate and a hydraulic cylinder reciprocated mounting plate supports a group of hypodermic needles in slidable registry with the front plate openings, which pierce a liquid absorbent web backing the front plate. Each needle is connected by a flexible tube to an adjustable stroke piston pump where inlets are connected to liquid injectable holding receptacles. The pistons are simultaneously actuated by a motor driven drive cam carrying shaft, the motor being controlled by a handle carried switch to rotate the shaft one turn. The shaft carrying cam also controls the flow of liquid to the handle cylinder, and the absorbent pad is connected to a source of antiseptic. A marking pad is carried by the handle front wall to identify the puncture area. Another form of handle includes a flexible band separably encircling the operator's hand for specialized field use.

14 Claims, 16 Drawing Figures

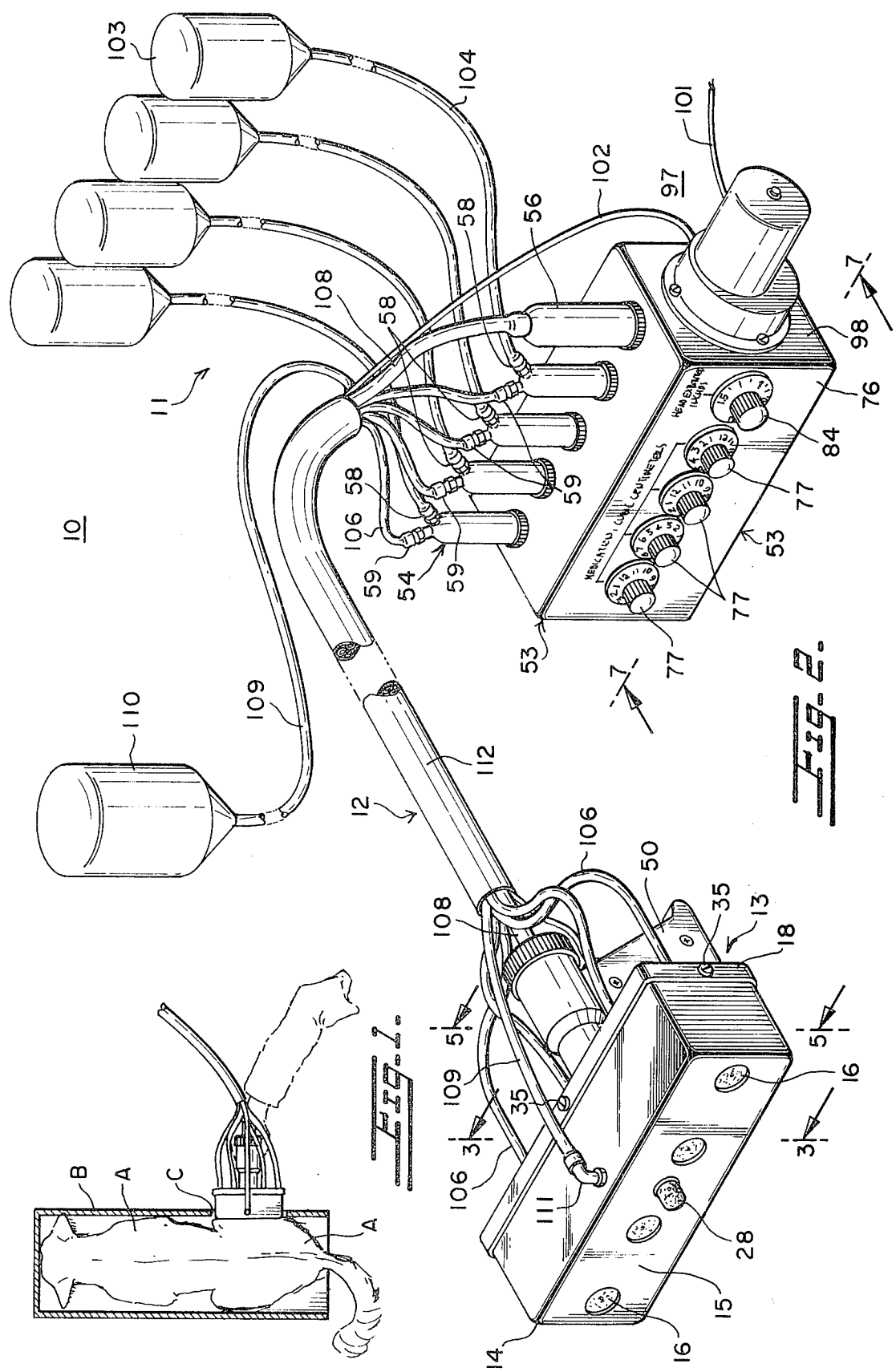

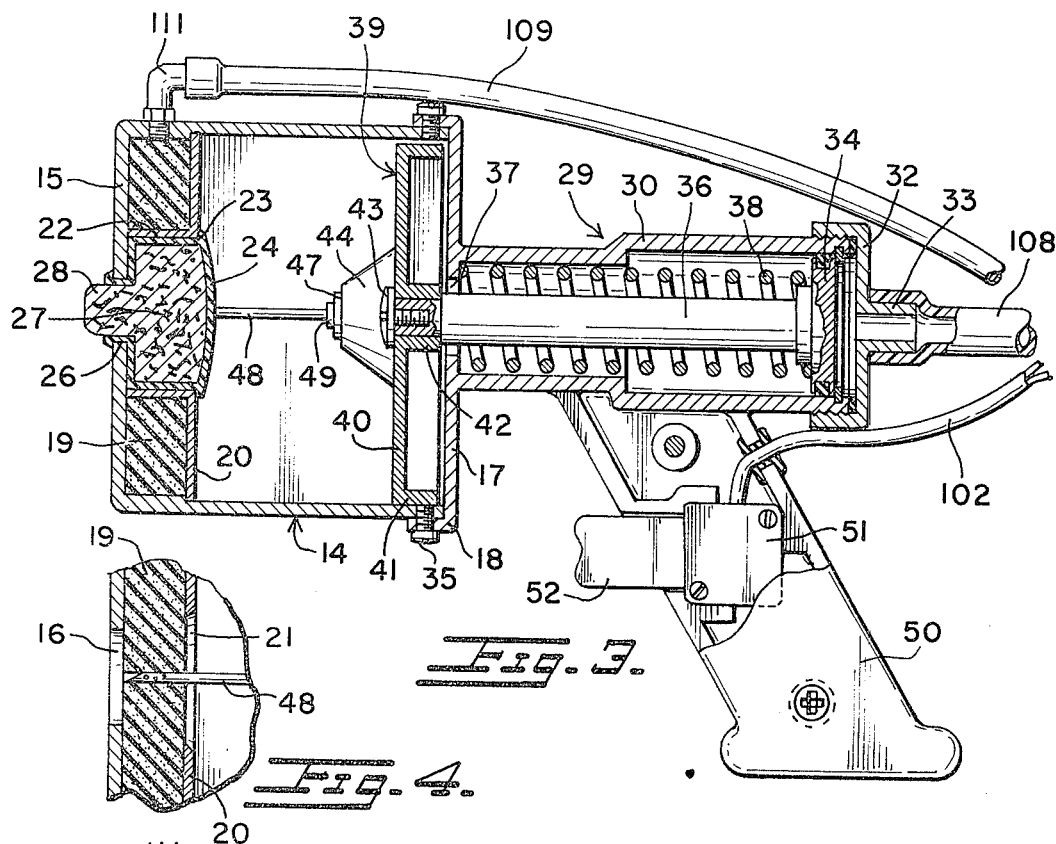
Fig. 3.
Fig. 4.
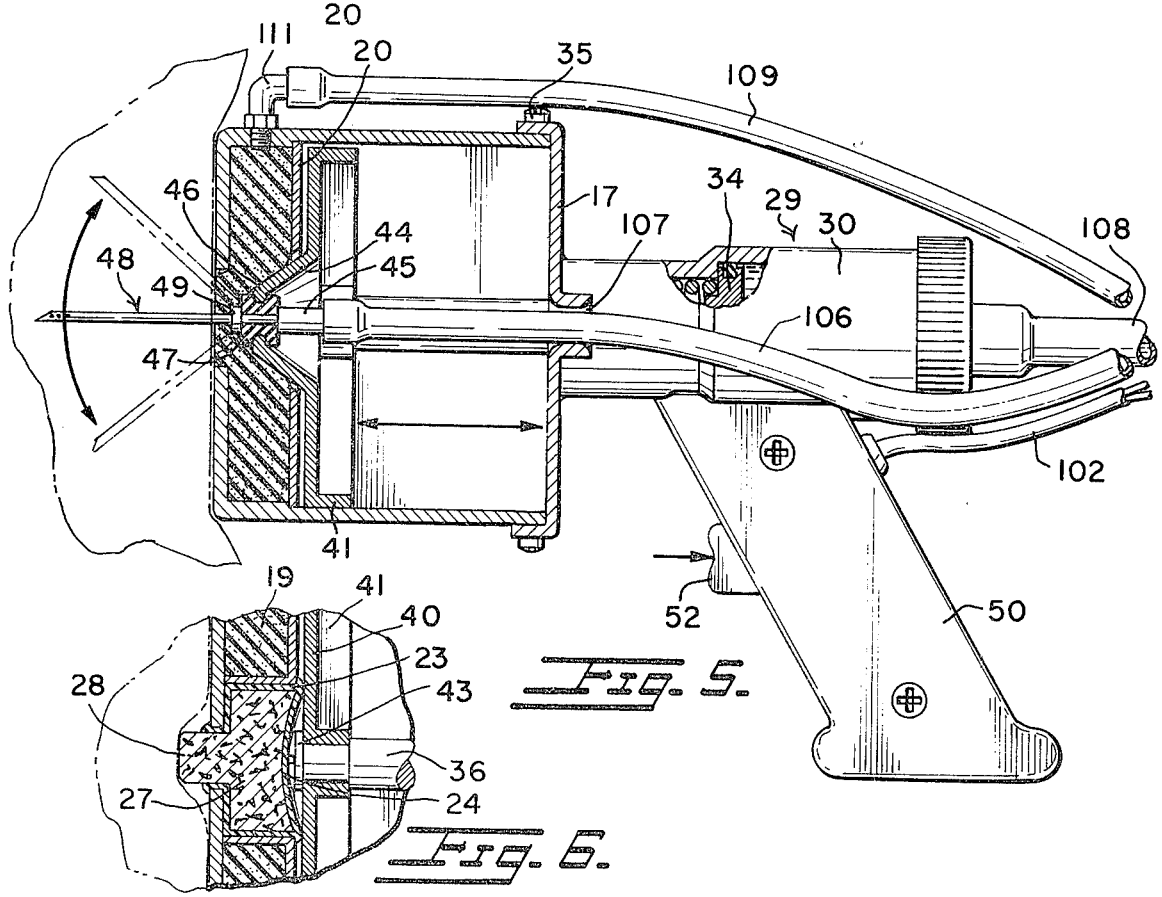
Fig. 5.
Fig. 6.

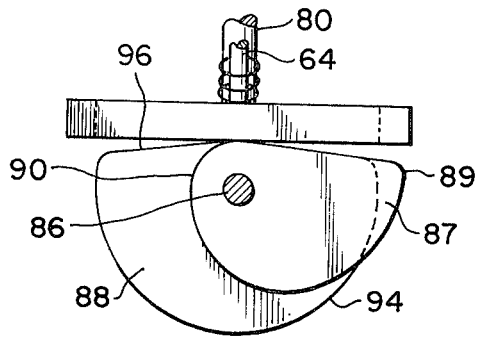
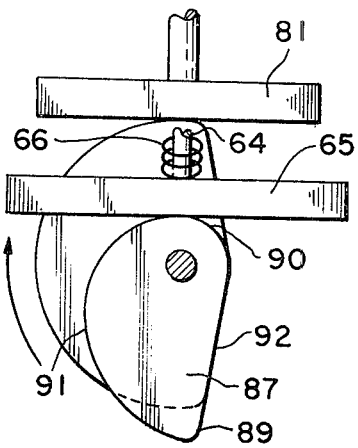
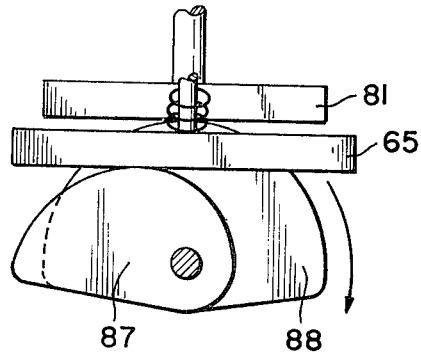
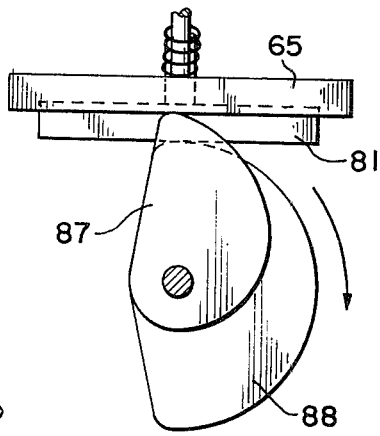
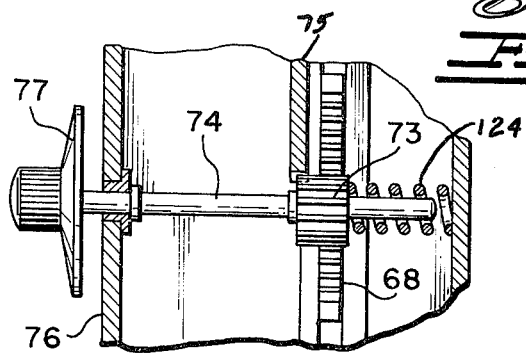
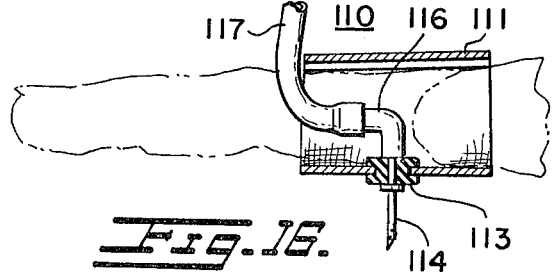
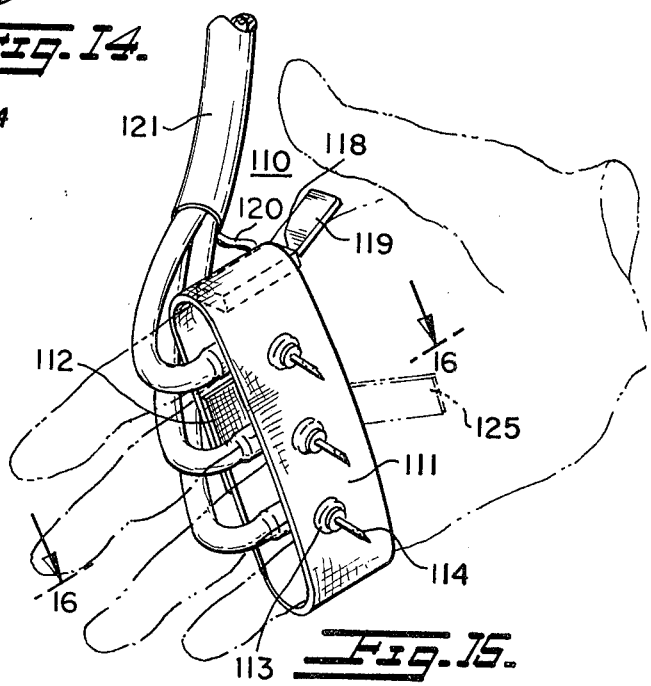

3,949,746

ANIMAL INJECTOR APPARATUS

BACKGROUND OF THE INVENTION

The present invention relates generally to improvements in animal medical devices and it relates more particularly to an improved apparatus for the administration of medicaments to animals by injection.

It is frequently desirable to administer to an animal a group of different medicaments by injection. However, the medicaments to be administered are frequently mutually incompatible and are accordingly necessarily separately injected. Since the administration of a single medicament to an animal by injection in the conventional manner possesses numerous drawbacks and disadvantages, it being highly time consuming and requiring the use of highly skilled labor, the separate administration by injection of a plurality of medicaments is many times more troublesome and timeconsuming by reason of the reaction of the animal to successive injections and the aggregate time required for the unit injections sometimes preventing the required dosage being given in the later injections occassioned by the irritability of the animal.

SUMMARY OF THE INVENTION

It is a principal object of the present invention to provide an improved medical device for animals.

Another object of the present invention is to provide an improved apparatus for injecting liquid medicaments into animals.

Still another object of the present invention is to provide an improved apparatus for simultaneously injecting into an animal a plurality of normally incompatible liquid medicaments.

A further object of the present invention is to provide an improved apparatus for simultaneously injecting a plurality of liquid medicaments of individually adjustable doses into an animal.

Yet another object of the present invention is to provide an improved apparatus for repetitively injecting a group of animals with a plurality of liquid medicaments safely and quickly with a minimum of pain for the animal and defusing the medicaments in the animal.

Still a further object of the present invention is to provide an apparatus of the above nature characterized by its high reliability, repetitiveness, wide adjustability, ruggedness, ease and convenience of use and great versatility and adaptability.

In a sense the present invention contemplates the provision of a multiple dose injection apparatus which comprises a group of longitudinally extending transversely spaced hypodermic needles supported by a common mount, a group of positive displacement liquid metering pumps having inlets connected to respective liquid injectable containing receptacles and outlets connected to respective needles and drive means for driving the pumps a unit cycle.

In accordance with a preferred form of the improved apparatus, the mount is hand held and includes a front wall backed by an antiseptic saturated absorbent pad pierced by the needles, the wall having openings registering with the needles. The needles are resiliently universally swingably mounted on a support plate which is reciprocated by a hydraulic drive cylinder which is actuated in synchronism with the driving of the pumps. Each of the pumps is a positive drive pump, such as a piston pump including inlet and outlet check valves and cooperating stop elements are provided on each pump piston rod and an associated adjustable rack to permit the individual adjustment of each piston stroke. The pumps are connected to the needles by flexible tubes and the slave cylinder is connected to a master cylinder proximate the pumps. A set of cams are mounted in a motor driven shaft, which drive the pump and master cylinder piston. According to another form of the present improved apparatus, the hypodermic needles are carried by a flexible band which can be separably applied to the hand of the operator.

The improved apparatus is highly reliable, easy and convenient to operate and adjust with a minimum of skill, is highly rugged and of great versatility and adaptability.

BRIEF DESCRIPTION OF THE DRAWINGS

FIG. 1 is a plan view, partially in section, illustrating the application of the improved apparatus to an animal;

FIG. 2 is a perspective view of an apparatus embodying the present invention;

FIG. 3 is an enlarged sectional view taken along line 3—3 in FIG. 2;

FIG. 4 is a fragmentary sectional view taken along a plane parallel to the plane of 3—3, the needles being illustrated in retracted position;

FIG. 5 is a sectional view taken along line 5—5 in FIG. 2;

FIG. 6 is a fragmentary view of FIG. 3 with the needles in their advanced positions;

FIG. 9 is a sectional view taken along line 9—9 in FIG. 8 with the cams shown in the pump and master cylinder retracted positions;

FIGS. 10–12 are views similar to FIG. 9 with the cams shown in successive positions in an operational cycle;

FIG. 13 is a sectional view taken along line 13—13 in FIG. 7;

FIG. 14 is a fragmentary perspective view of a tip of one of the hypodermic needles;

FIG. 15 is a perspective view of the injection section of another embodiment of the present invention; and FIG. 16 is a sectional view taken along line 16—16 in FIG. 15.

DESCRIPTION OF THE PREFERRED EMBODIMENTS

Figure 7:
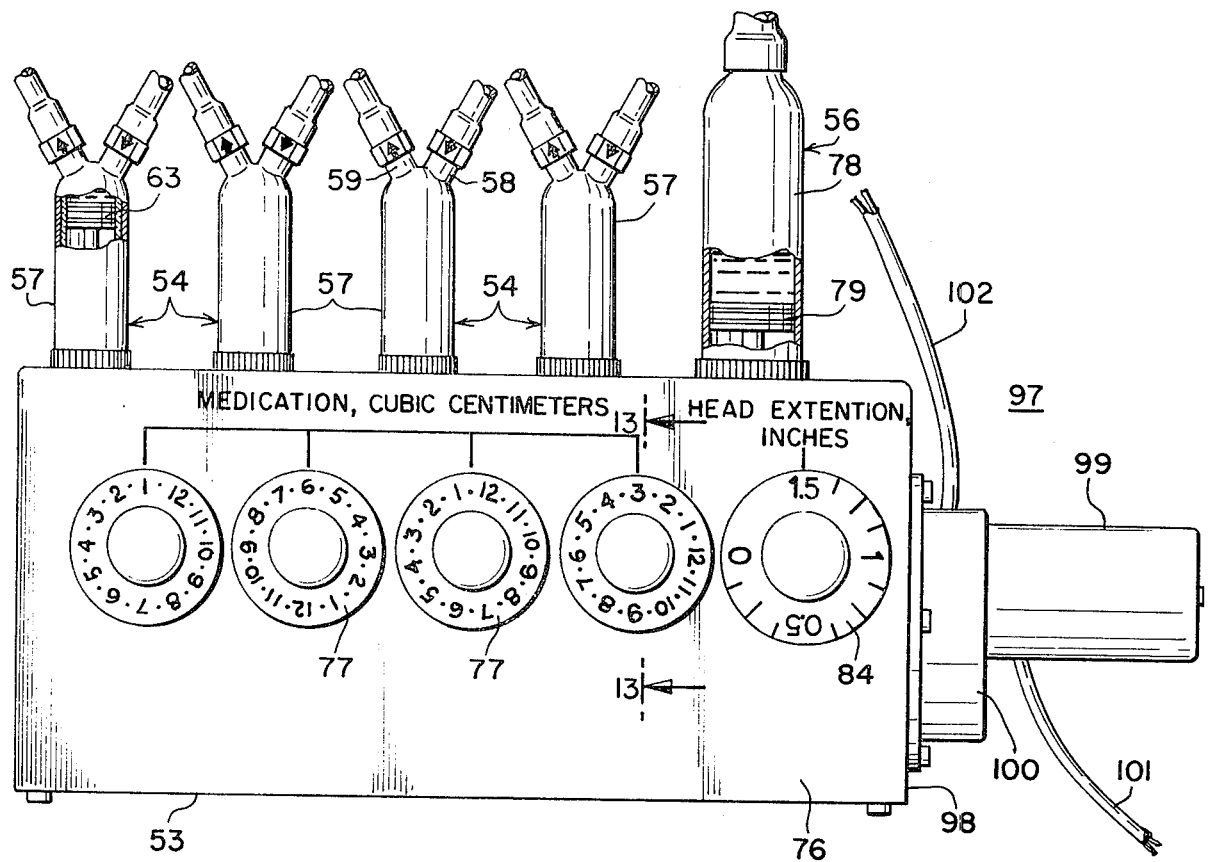
FIG. 7 is a front elevational view taken along line 7—7 in FIG. 2.

Referring now to the drawings, particularly FIGS. 1–14 thereof, which illustrate a preferred embodiment of the present invention, the reference numeral 10 generally designates the improved apparatus as applied to the simultaneous injection of four independently adjustable doses of liquid medicaments, it being understood that the apparatus may be readily modified for application to the simultaneous injection of more or less adjustable doses. The apparatus 10 includes a liquid medicament metering and control section 11 connected by a flexible elongated coupling assembly 12 of feed tubes and control conductors to a hand held medicament injection section 13. While section 13 is illustrated as hand held, it could be mounted on a wall of a stall or passageway for the animals to be treated.

The injection section comprises a front housing 14 shown as rectangular, including a laterally extending front wall 15 having four regularly longitudinally spaced vertically medially disposed circular openings 16 and a rectangular rear wall 17 provided with a peripheral flange 18 engaging the border of the peripheral wall of housing 14 and secured thereto by screws 35. The front wall 15 is backed by a soft, compressible, pierceable, liquid absorbant pad 19 which may be formed of artificial or synthetic sponge material and is saturated with an antiseptic liquid which may be of any suitable well known type. The pad 19 is secured in position by an intermediate backing plate 20, which with front wall 15, defines a pad housing chamber, the backing plate 20 being provided with circular openings 21 coaxial with respective openings 16 as seen best in FIG. 4, and a centrally disposed integrally formed collar 22 projecting forwardly into engagement with front wall 15, as seen best in FIG. 3.

Telescoping the collar 22 is a cylindrical container 23 having a rearwardly convex, resilient, flexible rear wall 24 and a forwardly projecting sleeve 26 engaging a circular coaxial opening in front wall 15 and secured thereto. The container 23 snugly houses a felt body member 27 which is saturated with a marking ink of any desired color and has a coaxial tongue or applicator 28 projecting through and forwardly of sleeve 26.

An actuating cylinder 29 includes a hollow cylindrical body 30 which is integrally formed with and projects centrally rearwardly from rear wall 17 and is closed at its rear by a screw cap 32 having a short coaxial, integrally formed coaxial nipple 33. A piston 34 having a suitable packing ring slidably hermetically engages the inside face of cylinder body 30 and a piston rod 36 projects coaxially forwardly from piston 34 through a coaxial opening 37 in rear wall 17. A helical compression spring 38 encircles piston rod 36 and is entrapped between the confronting faces of rear wall 17 and piston 34 to urge the latter to its retracted position.

As seen best in FIGS. 3 and 5, piston rod 36 supports at its front end in housing 14, a needle mount 39 which includes a rectangular panel 40 having a peripheral flange 41, the lower and side legs of which slidably engage the peripheral inside faces of housing 14 and the upper leg of which is spaced from the housing top wall. The mount 39 is secured to piston rod 36 by a collar 42 integrally formed with panel 40 and engaging the free end of rod 36 and a suitable locking screw 43.

Integrally formed with the mount panel 40 are forwardly directed tubular conical projections 44 which are coaxial with respective openings 16 and provide at their front openings with inwardly directed flanges 46. As seen best in FIG. 5, an elastomeric grommet 47 is coaxial with and firmly fixed in the front end opening of each projection 44 and is encircled and engaged by the flange 46. A hypodermic needle 48 coaxially projects through each grommet 47 and is locked thereto by a front annulus 49 formed on the needle 48 and enlarged rear coupling tube or sleeve 45 of the needle sandwiching the grommet so that the needle 48 is universally swingable about its proximal end as shown in FIG. 5, and is biased perpendicular to panel 40. The angular movement of needle 48 allows the animal to move without danger of needle breakage. The distal end of the needle 48 is bevelled in the known manner and is provided in its wall proximate the tip with a plurality of small openings 49 as seen best in FIG. 14, to expedite the injection of the liquid medicament into the animal coaxially and laterally.

Formed with and depending from the cylinder body 30 is a suitably shaped handle or grip 50 which houses a normally open control switch 51. The switch 51 is actuated by a plunger or trigger member 52 extending from switch 52 forwardly through an opening in hand grip 50.

The metering section 11 includes a rectangular drive housing cabinet 53 on the top wall of which are mounted four piston type metering pumps 54 and a master cylinder 56. As seen best in FIGS. 7 and 8, each of the pumps 54 includes a vertical hollow cylinder 57 secured to the cabinet top wall and inlet and outlet nipples 58 and 59 respectively connected with the top of cylinder 57 and housing check valves 60 and 61 respectively, the check valve 60 allowing liquid flow only into the cylinder 57 and the check valve 61 allowing liquid flow only out of the cylinder 57.

Figure 8:
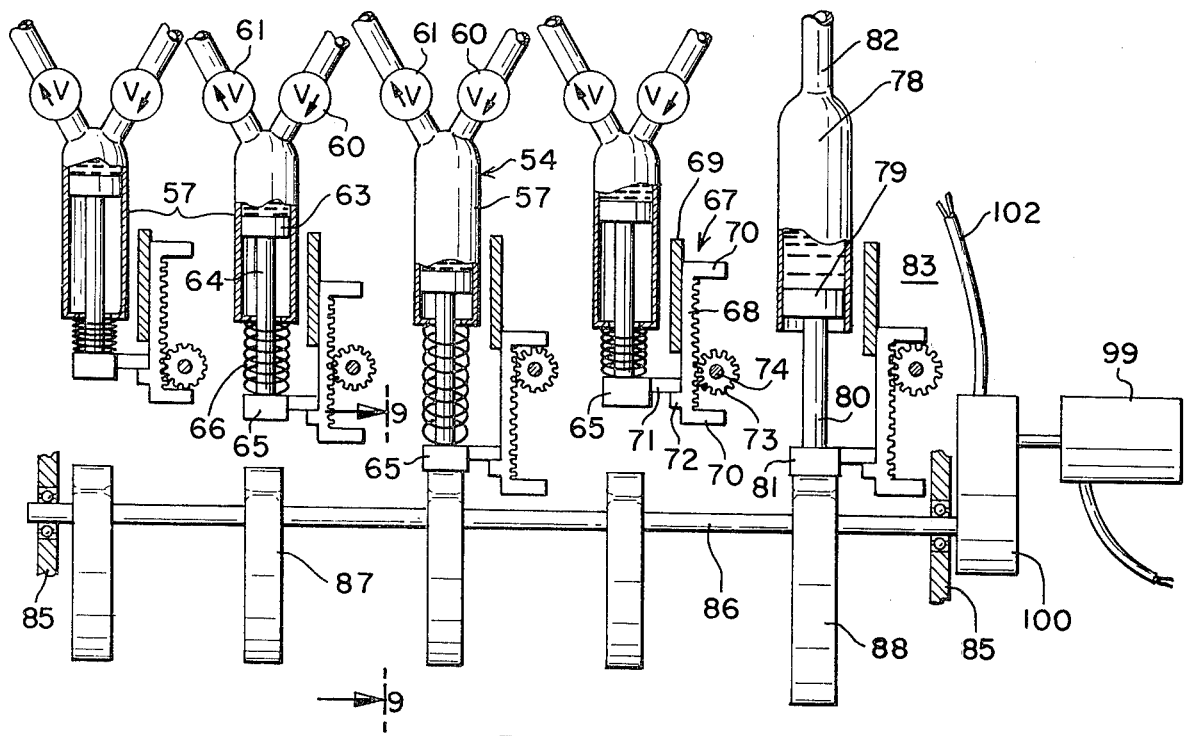
FIG. 8 is a fragmentary front elevational view, partially in section, of the pump and pump drive mechanism.

As seen in FIG. 8, a piston 63 is reciprocatable in each of the cylinders 57 and is provided with a coaxial depending piston rod 64 which projects through an opening in the bottom of the cylinder 57 into cabinet 53. Each piston rod 64 terminates at its bottom in a follower defining enlarged head 65 and the piston 63 and piston rod 64 are resiliently urged to their retracted lowered position by a helical compression spring 66 encircling the piston rod 64 and entrapped between the head 65 and the cylinder 57 bottom end wall.

As seen best in FIG. 8, a mechanism 67 is provided with each of the pumps 54 for independently adjusting the stroke of the piston 63 thereof and hence the discharge per cycle. Each adjustment mechanism 67 includes a vertically movable linear rack 68 slidable along a guide plate 69 and provided at opposite ends with perpendicular arms 70 limiting its vertical movement. Projecting laterally from the follower head 65 on a respective piston rod is a first stop element 71 and a second stop element 72 projects laterally from the tack 68 into the path of and below the stop element 71. Thus, by raising and lowering the rack 68 the respective piston stroke is adjusted.

A pinion 73 engages each rack 68 and is affixed to a suitably journalled shaft 74 projecting through the front wall 76 of cabinet 53. Mounted to each shaft 74 in front wall 76 is a suitably graduated knob 77. As shown in FIG. 13, knob 77 is fixed in position by a locking key 75 interfitting the teeth of pinion 73, when knob 77 is released and urged into rest position by spring 124.

The master bylinder 56 includes a cylinder body 78 mounted on the cabinet top wall and a reciprocatable piston 79 is disposed in cylinder 78 and provided with a depending piston rod 80 terminating in an enlarged follower defining head 81. The top of cylinder 78 terminates in a coupling nipple 82. A mechanism 83 is provided for adjusting the stroke of the piston 79 and is similar to the mechanism 67 described above and includes an adjustment knob 84 at the cabinet front wall 76.

In order to actuate the pumps and master cylinder there is provided a transversely extending shaft 86 journalled by ball bearings 85 suitably supported in cabinet 53 below the pumps and master cylinder. Affixed to the shaft 86 and registering with the follower heads 65 are first cams 87 which are of similar shape and similarly positioned or phased on the shaft 86. Also affixed to shaft 86 and registering with follower 81 is a second cam 88. As seen best in FIGS. 9–12, each of the first cams 87 include a raised portion 89 and an opposite depressed portion 90 joined by oppositely disposed curved and straight portions 91 and 92 respectively. The cam 88 includes a circular raised portion or land 94 extending about 180° and a depressed portion 96. The cams 87 and 88 are so phased upon shaft 86 that upon rotation of the shaft 86 the cam land 94 of cam 88 engages follower head 81 just before the rise portion 91 of cam 87 engages follower head 65 almost concurrently with the disengagement of follower 65 by raised portion 89.

The shaft 86 is driven by a single revolution drive assembly 97 mounted on an end wall 98 of cabinet 53. The assembly includes a drive motor 99 mounted to and connected by way of a speed reduction gear train to the input of a suitably housed single revolution electrically controlled clutch unit 100 whose output is coupled to the shaft 86. The drive assembly 97 is connected by a conductor line 101 to a source of current and for control purposes by a conductor line 102 to the switch 51.

A group of bottles 103, each containing a different liquid medicament to be injected, are suitably supported in inverted condition above the level of the pumps 54 and are connected to the pump inlets 58 by flexible tubes 104. The outlets 59 of pumps 54 are connected by highly flexible, thick wall, corrosion and pressure resistant tubes 106 to respective hypodermic needles 48, each of the tubes 106 entering a flanged opening 107 in the housing rear wall 17 and engaging the proximal feed sleeve 45 of a respective hypodermic needle 48. The master cylinder outlet nipple 82 is connected by a thick walled flexible hose 108 to the actuating cylinder inlet nipple 33. Another flexible tube 109 connects a suitably supported liquid antiseptic containing inverted bottle 110 to the pad housing chamber in front housing 14 by way of an angle coupling 111 communicating with the upper part of the chamber. The line 102 and tubes 106, 108 and 109 are bunched together and enclosed along their length by a thin flexible sheath 112 to form a harness.

In employing the apparatus 10 described above, the knobs 77 and 84 are adjusted to central respectively the strokes of the metering pumps so as to effect the desired doses of the respective injectibles and to control the stroke of the master cylinder piston and hence that of the hypodermic needles. An animal A is positioned in a pen B as seen in FIG. 1, having an open end and provided with an opening C in a side wall exposing the area of the animal to be injected. The operator merely presses the front wall 15 of unit 10 through opening C against the animal and presses the trigger 52 to inject and mark the animal.

Upon closure of the switch 51 with the pressing of trigger 52 the drive assembly 97 is actuated to rotate shaft 86 a single revolution. The rest or dormant positions of the shaft and drive cams are shown in FIG. 9. At the initial part of the shaft cycle (FIG. 10), the cam 88 raises the follower head 81 and piston 79 to pump hydraulic fluid into sleeve cylinder 29 to advance the piston 34, mount 39 and needles 48, an amount controlled by the adjustment of knob 84. The needles 48 advance to enter the animal A and, as seen in FIG. 6, the head of screw 43 bears on flexible wall 24 to compress it and urge ink from pad applicator 28 to mark the animal. Upon further rotation of the shaft and cams, as seen in FIG. 11, the piston 79 is retained in its raised position by the raised land 94 and the hypodermic needles 48 remain advanced whereas the curved incline cam portions 91 on cam 87 engage and slowly raise followers 65 to raise pistons 63 and pump the liquid medicaments into the animal A through respective needles 48 in amounts determined by the adjustment of the bottoms of the piston strokes. Following the end of the cycle (FIG. 12) the raised portions of cams 87 and 88 travel past their corresponding followers to permit their return to the positions shown in FIG. 9 to complete the cycle. With the return of pistons 63 the pump cylinders draw new charges from the bottles 103 and with the release of follower 81 the piston 34 is retracted under the influence of spring 38 to withdraw and retract the needles 48. As the needles traverse the pad 19, they are wiped by the pad 19 and have antiseptic applied thereto to accordingly sterilize the needles for subsequent applications. The above cycle of operation may be repeated merely by again pressing the switch trigger 52.

Referring now to FIGS. 15 and 16 of the drawings which illustrate a modified form of applicator in which the automatic needle advances, marking and antiseptic operations are eliminated. This unit is intended for injecting swine and similar animals in certain awkward locations in the pens or yards. The reference numeral 110 illustrates the improved applicator which includes a flexible preferably fabric band 111 having mating separable fasteners 112, for example hook and eye areas, at their opposite ends, so as to permit the easy encircling of the hand of the operator. A plurality of longitudinally spaced, transversely medially positioned elastomeric grommets 113 project through and are received to the band 111. A short hypodermic needle 114, having a tip construction as shown in FIG. 14 is firmly resiliently supported by and projects through each grommet 113 and terminates at its inner end in an angle coupling 116 connected by a flexible tube 117 to a metering pump correspondingly to pump 54, earlier described. Also carried by the band 111, either at its side or along the palm of the operator is a central switch 118 including an actuating arm 119. The switch 118 is connected to the driving and cycling mechanism, corresponding to mechanism 97 by a line 120 and tubes 117 being bunched and enclosed in a flexible sheath 121. If desired, an automatic switch unit could be used, actuated by an arm 125, which is angled to be pivotted when the palm is pressed against the animal.

The operation of the device 110 with its associated components is similar to that of apparatus 10. In application, the operator merely manually inserts the group of needles 114 into the animal and depresses the actuator arm 119 to motivate the metering pumps for one cycle to effect the injection of the medicaments and be then withdraws the needles.

While the front face of unit 10 was shown rectangular, circular faces with the needles spaced along the circumference of a circle can be provided.

Also, the knobs 77 may be set to "0" to have no movement of the corresponding piston, so that no predicament will flow. Also while all the needles move in unison by being mounted on a single piston, each could be separately mounted if desired, controlled by separate units 56. While one knob 77 locking construction was illustrated, others may be used such as a pin on knob 77 engaging a detent on a plate. The detents correspond to linear positions on the racks 68.

While there have been described and illustrated preferred embodiments of the present invention, it is apparent that numerous alterations, omissions and additions may be made without departing from the spirit thereof.

What is claimed is:

1. A multiple dose injection apparatus comprising a plurality of longitudinally extending hypodermic needles, hand manipulatable common mount supporting said needles, a liquid feed station remote from said support which is freely movable relative to said station, said station comprising a plurality of liquid metering means having repetitive cycles, means including a flexible tube connecting the outlet of each of said metering means to a respective hypodermic needle, a plurality of receptacles for holding liquids and communicating with the inputs of respective metering means, means for actuating said metering means a predetermined cycle, means for forcing said liquids through said needles and means for individually adjusting the output of each of said metering means for said predetermined cycle.

2. The apparatus of claim 1 wherein said metering means and forcing means is a positive displacement pump.

3. The apparatus of claim 2 wherein each of said pumps comprises a cylinder, a piston reciprocatable in said cylinder, a first check valve at the inlet to each pump preventing the flow of liquid from said cylinder and a second valve at the outlet from each pump preventing the flow of liquid into said cylinder.

4. The apparatus of claim 3 wherein, said adjusting means includes means for individually adjusting the strokes of said pistons.

5. The apparatus of claim 3 wherein each of said pumps includes a spring urging the respective piston to a retracted position and a piston rod extending from the piston and terminating in a follower element, said pump actuating means including a shaft, motor means driving said shaft and a plurality of cams mounted in and rotatable with said shaft and engagable by respective followers whereby a single rotation of said shaft effects a single reciprocation of said pistons.

6. The apparatus of claim 4 wherein said adjusting means includes a first stop member carried by each of said piston rods, a second stop member located in the path of each of said first stop member and means for individually adjusting the portion of each of said second stop members along the paths of the respective first stop members.

7. The apparatus of claim 1 wherein said actuating means comprises an electric motor and means including a manually operable control switch mounted on said support for connecting said motor to a source of current and driving said pumps.

8. The apparatus of claim 1 wherein said mount includes means supporting said hypodermic needles for universal swinging about their proximal ends and resiliently bearing said needles along longitudinal mutually parallel directions.

9. The apparatus of claim 1 wherein said mount comprises a mounting plate supporting said needles in transversely spaced forwardly projecting positions, a front plate disposed forwardly of said mounting plate and having openings therein registering with respective hypodermic needles and means for reciprocating said mounting plate between retracted and advanced positions with said needles being withdrawn rearwardly and advanced forwardly of said front face respectively.

10. The apparatus of claim 9 including an intermediate plate disposed between said front plate and said mounting plate and having openings therein registering with said needles, and a liquid absorbent pad sandwiched between said front and intermediate plates and pierced by said needles.

11. The apparatus of claim 1 wherein said mount comprises a hand encircling band.

12. The apparatus of claim 1 wherein said needles have openings on the side wall adjacent the free end.

13. A multiple dose injection apparatus comprising a plurality of longitudinally extending hypodermic needles, a common mount supporting said needles, a plurality of liquid metering means having repetitive cycles, means connecting the outlet of each of said metering means to a respective hypodermic needle, a plurality of receptacles for holding liquids and communicating with the inputs of respective metering means, means for actuating said metering means a predetermined cycle and means for forcing said liquids through said needles, said mount comprising a mounting plate supporting said needles in transversely spaced forwardly projecting positions, a front plate disposed forwardly of said mounting plate and having openings therein registering with respective hypodermic needles and means for reciprocating said mounting plate between retracted and advanced positions with said needles being withdrawn rearwardly and advanced forwardly of said front face respectively said reciprocating means comprising a cylinder carrying said front plate a piston reciprocatable in said cylinder and connected to said mounting plate and means connecting said cylinder to a controlled source of pressurized fluid.

14. A multiple dose injection apparatus comprising a plurality of longitudinally extending hypodermic needles, a common mount supporting said needles, a plurality of liquid metering means having repetitive cycles, means connecting the outlet of each of said metering means to a respective hypodermic needle, a plurality of receptacles for holding liquids and communicating with the inputs of respective metering means, means for actuating said metering means a predetermined cycle and means for forcing said liquids through said needles, said mount comprising a mounting plate supporting said needles in transversely spaced forwardly projecting positions, a front plate disposed forwardly of said mounting plate and having openings therein registering with respective hypodermic needles and means for reciprocating said mounting plate between retracted and advanced positions with said needles being withdrawn rearwardly and advanced forwardly of said fron face respectively, said front plate having an additional opening formed therein and including a chamber disposed behind said additional opening and having a compressible rear wall in the path of said mounting plate and a front opening registering with said additional opening and a compressible liquid absorbent pad housed in said chamber and projecting through said front opening.

* * * * *

UNITED STATES PATENT OFFICE
CERTIFICATE OF CORRECTION

Patent No. 3,949,746          Dated April 13, 1976.

Inventor(s)  Mark Wallach

It is certified that error appears in the above-identified patent and that said Letters Patent are hereby corrected as shown below:

| Claim | Line | |
|---|---|---|
| 6 | 5 | Change "portion" to -- position -- |
| 7 | last line | Change "pumps" to -- liquid metering means -- |

Signed and Sealed this

Ninth Day of November 1976

[SEAL]

Attest:

RUTH C. MASON  
Attesting Officer

C. MARSHALL DANN  
Commissioner of Patents and Trademarks